(12) United States Patent
Leslie et al.

(10) Patent No.: US 9,724,428 B2
(45) Date of Patent: Aug. 8, 2017

(54) MEDICAL DEVICES FOR COLLECTING PATHOGENIC CELLS

(71) Applicant: Cook Medical Technologies LLC, Bloomington, IN (US)

(72) Inventors: Julia E. Leslie, League City, TX (US); Andrew K. Hoffa, Bloomington, IN (US); Tyler J. Bunch, Bloomington, IN (US); Sean Chambers, Bloomington, IN (US); Colleen Gemborys, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/458,651

(22) Filed: Aug. 13, 2014

(65) Prior Publication Data
US 2014/0348860 A1 Nov. 27, 2014

Related U.S. Application Data (63) Continuation of application No. PCT/US2013/025895, filed on Feb. 13, 2013.

(60) Provisional application No. 61/597,939, filed on Feb. 13, 2012.

(51) Int. Cl.

| | |
|---|---|
| *A61K 39/395* | (2006.01) |
| *A61F 2/00* | (2006.01) |
| *A61K 47/48* | (2006.01) |
| *A61L 29/08* | (2006.01) |
| *A61L 29/16* | (2006.01) |
| *A61L 31/04* | (2006.01) |
| *A61L 31/08* | (2006.01) |
| *A61L 31/16* | (2006.01) |
| *A61K 9/00* | (2006.01) |
| *A61F 2/01* | (2006.01) |
| *A61K 39/00* | (2006.01) |

(52) U.S. Cl.
CPC .......... *A61K 47/48992* (2013.01); *A61F 2/01* (2013.01); *A61K 9/0024* (2013.01); *A61K 39/39558* (2013.01); *A61L 29/08* (2013.01); *A61L 29/16* (2013.01); *A61L 31/047* (2013.01); *A61L 31/08* (2013.01); *A61L 31/16* (2013.01); *A61F 2002/016* (2013.01); *A61F 2250/0067* (2013.01); *A61K 2039/505* (2013.01); *A61L 2300/252* (2013.01); *A61L 2300/404* (2013.01); *A61L 2300/606* (2013.01)

(58) Field of Classification Search
None
See application file for complete search history.

(56) References Cited

U.S. PATENT DOCUMENTS

| | | | |
|---|---|---|---|
| 2003/0229393 A1 | 12/2003 | Kutryk et al. | |
| 2009/0123516 A1* | 5/2009 | Agrawal | A61K 47/48046 514/1.1 |
| 2012/0259401 A1* | 10/2012 | Gerrans et al. | 623/1.11 |

OTHER PUBLICATIONS

Bioinspired multivalent DNA network for capture and release of cells, Zhao et al., PNAS, 19626-19631, Nov. 27, 2012, vol. 109, No. 48.
International Search Report and Written Opinion issued in PCT/US2013/025895, Jun. 24, 2013.
Nanoroughened Surfaces for Efficient Capture of Circulating Tumor Cells without Using Capture Antibodies, Chen et al., acsNANO, Articles ASAP, Nov. 29, 2012.
Nanoroughened Surfaces for Efficient Capture of Circulating Tumor Cells without Using Capture Antibodies, Chen et al., acsNANO, vol. 7, No. 1, 566-575, 2013.
Faitas, Targeting Hematogenous spread of circulating tumor cells by a chemotactic drug-eluting IVC filter to prevent pulmonary and systemic metasis, Medial Hypotheses 74 (2010) 668-669.
Web pages www.news.cornell.edu/stories/208/12/device, Gold, "Researcher invents lethal 'lint brush' to capture and kill cancer cells in the bloodstream," Cornell Chronical, printed Apr. 15, 2016, 2 pages.

\* cited by examiner

*Primary Examiner* — Susan Tran
(74) *Attorney, Agent, or Firm* — Woodward, Emhardt, Moriarty, McNett & Henry LLP

(57) ABSTRACT

Disclosed is a medical device constructed and arranged for contact with a flow of blood or other bodily fluid of a patient and including an attached binding agent or a roughened surface that binds to pathogenic cells targeted for elimination from the blood or other bodily fluid. Also disclosed are methods for making and using the device.

21 Claims, 5 Drawing Sheets

MEDICAL DEVICES FOR COLLECTING PATHOGENIC CELLS

REFERENCE TO RELATED APPLICATION

The present application is a continuation of and claims the benefit of International Application Serial No. PCT/US2013/025895 filed Feb. 13, 2013, which claims the benefit of U.S. Provisional Patent Application Ser. No. 61/597,939 filed Feb. 13, 2012 entitled "MEDICAL DEVICES FOR COLLECTING PATHOGENIC CELLS", each of which is hereby incorporated by reference in its entirety.

BACKGROUND

The present invention relates generally to medical treatments and devices, and in certain forms to medical devices that are implantable in a vascular, lymphatic, or other bodily vessel or that otherwise contact patient bodily fluid and that collect unwanted cells circulating with bodily fluid, especially cancer cells, and to methods employing the same.

Cancer therapy is faced with a number of challenges. One of those is metastasis, in which a malignant tumor can be formed at a location distant from a primary tumor. Often, even if a primary lesion is successfully treated by surgical obliteration or otherwise, overall treatments are complicated and increased mortality rates are experienced due to the growth of tumors that have metastasized to other organs.

Metastasis is a complex process. It is thought to involve multiple steps, including release of malignant cells from the primary neoplasm, migration of cancer cells into circulation, adhesion at distant sites, and growth of the disseminated cancer cells within the vessels or within the tissue following extravasation. The prevention of metastasis by impacting one or more of these processes has become an important goal in cancer therapy. In some work, drugs that can be administered to inhibit metastatic disease have been explored. These drugs may for example inhibit intravasation of metastatic cells by elaborating a physical barrier or inhibit the ability of cancer cells to migrate. Satisfactory anti-metastatic treatments have, however, proven difficult to find.

In view of the background in this area, needs remain for improved and/or alternative means for treating cancer or other pathogenic processes in patients, including those that may be used to reduce or prevent the spread of disease in the patients. Aspects of the present invention are addressed to these needs.

SUMMARY

The present disclosure presents vascular or other implants or other devices that are capable of collecting and potentially facilitating the eradication of blood-borne or other bodily fluid-borne pathogenic cells such as cancer cells. Implants can be deployed permanently or temporarily in the vasculature system and/or another bodily fluid flow-supporting system and/or in an artificial blood or other bodily fluid flow circuit, and can in certain embodiments be coated with agents that bind to pathogenic cell surface molecules such as proteins. Blood-borne or other bodily fluid-borne pathogenic cells that pass near the device are captured on the device, and can subsequently be irradiated to kill them or otherwise removed from the blood or other bodily fluid flow.

Additional aspects of the disclosure as well as features and advantages thereof will be apparent from the further descriptions herein.

DETAILED DESCRIPTION

Reference will now be made to certain embodiments and possible variations thereof and specific language will be used to describe the same. It should nevertheless be understood that no limitation of the scope of this disclosure and the claims is thereby intended, and that such alterations, further modifications and further applications of the principles described herein are contemplated as would normally occur to one skilled in the art to which the disclosure relates. In several figures, where there are the same or similar elements, those elements are designated with the same or similar reference numerals.

As disclosed above, in certain of its aspects, the present invention relates to medical implants capable of localizing blood borne and/or other bodily fluid borne pathogenic cells such as cancer cells, and to related methods of preparation and of use, e.g. to kill or otherwise eliminate the cells from a patient. For these purposes the medical implant can have a coating that includes an agent that binds to the pathogenic cells, for example by binding to a biologic molecule of the cell such as a protein located on the outer surface of the cell.

The device in accordance with the invention may be any of a wide variety of implant structures adapted for temporary or permanent implantation in any body passage including any epithelial lined vessel lumen that transports bodily fluid, for example, in a blood passage, such as a vessel or chamber, of the cardiovascular system or a vessel of the lymphatic, bile, urinary or other fluid flow system of a human or animal patient through which blood or other bodily fluid travels. The passage may for example be a tubular passage such as an artery or vein or duct, or may be a larger chamber such as a ventricle or atrium of the heart. Implants that span or bridge cardiovascular passages are also contemplated. The implant can be adapted to be entirely or only partially implanted in the blood or other bodily fluid passage. The device may also be a structure which is a part of or which can be deployed within an extracorporeal blood circuit or other extracorporeal bodily fluid flow circuit. In addition to the vascular system, other bodily fluid transport systems suitable for the present invention include, but are not limited to, lymphatic vessels or ducts, vessels of the urinary system such as the ureter, and bile ducts, including the common bile duct. In certain aspects, two or more implants as described herein can be implanted at different locations within a given bodily fluid transport system, including any such system described herein. Further, in additional aspects, separate implants as described herein can be implanted in two or more bodily fluid flow systems and can reside in those systems simultaneously so as to provide the capacity for simultaneous removal of cancer or other pathogenic cells from those two or more systems. Illustratively, a first such implant can be implanted in a vessel of the lymphatic system, and a second such implant can be implanted in a vessel of at least one other bodily fluid flow system, for example the vasculature, the urinary tract, or a bile duct. The implants and/or the coatings or roughened surfaces on such implant can be the same or can differ from one another in these embodiments.

Implant devices such as those described herein for vascular or other bodily system introduction can also be introduced within a tubular passage of an extracorporeal blood or other bodily fluid circuit. Additionally or alternatively, the inner lumen of an artificial tubular passage in an extracorporeal blood or other bodily fluid circuit can be partially or completely coated with a binding agent as described herein to provide a pathogenic cell-capturing function as described herein.

By way of example, an implant for use herein can be a catheter, a wire guide, a stent, a coil, a needle, a graft, a filter, a balloon, particles which circulate in the blood or other bodily fluid and which can be captured or which are excreted, an implantable porous body that allows passage of the subject bodily fluid, or any combination of these, and/or the implant can be configured to be retrievable after a period of implantation in a patient (e.g. with the inclusion of a hook, ball or other structure that can be captured with a snare or other retrieval device and forced back into a cannula for withdrawal from the patient). Suitable catheter types include for example central venous catheters and peripherally inserted central catheters. Suitable filters include for example vena cava filters such as the Cook Celect® and Cook Günther Tulip® and Cook Gianturco-Roehm Bird's Nest® filters available from Cook Incorporated, Bloomington Ind., USA. Suitable stents include those without a sheath covering, for example the Cook Zilver® stent available from Cook Incorporated. Suitable stents also include those with a sheath covering, such as a sheath-covered stent that can be used in a transjugular intrahepatic portosystemic shunt (TIPS) procedure wherein the stent structure and/or sheath can carry the binding agent as disclosed herein and effectively capture live cancer cells. A sheath, if present on a stent or other implant, preferably carries the binding agent so as to present the binding agent on an inner, blood-exposed lumen surface of the sheath. This can be accomplished by coating the binding agent on the inner lumen surface of the sheath or by impregnating the sheath material with the binding agent, for instance. Stents with or without a sheath covering can be retrievable for example as described in International Patent Application Publication No. WO2006119144 dated Nov. 9, 2006 (Wilson-Cook Medical, Inc.), or can remain attached to a retrieval structure such as a wire throughout the period of implantation, for example as described in U.S. Patent Application Publication US20090143851 dated Jun. 4, 2009 (publishing U.S. patent application Ser. No. 12/324,484 filed Nov. 26, 2008) and U.S. Patent Application Publication US20100168837 dated Jul. 1, 2010 (publishing U.S. patent application Ser. No. 12/721,323 filed Mar. 10, 2010), each of which is hereby incorporated herein by reference. Suitable coils include embolization coils. Suitable wire guides include for instance traditional wire guides as well as wire guides with an attached expandable structure for expansion within a blood vessel lumen, such as a coil, where the expandable structure can carry the attached binding agents as disclosed herein. Illustrative such devices are described for example in International Patent Application Publication No. WO2011140177 dated Nov. 10, 2011 (Cook Medical Technologies, LLC), which is incorporated herein by reference. An implantable porous body such as a resorbable or non-resorbable foam body that spans the lumen of the vessel in which it is implanted and allows passage of the bodily fluid through the porous body may be used, and may find particular use in vessels of systems with lower required flow such as vessels of bodily fluid systems other than the vasculature, for example the lymphatic system. Pathogenic cell binding agents as described herein can be applied to external surfaces of such porous bodies and/or within such porous bodies, e.g. such agents can be homogeneously or heterogeneously distributed through the porous bodies. These or other implants, in certain preferred embodiments, have at least a portion that is configured to expand during deployment so as to contact walls of the blood passage or other bodily fluid passage to anchor within the blood passage or other bodily fluid passage. In this regard, both self-expanding and force-expandable (e.g. balloon-expandable) implants are contemplated as being within the scope of embodiments of the present invention. As well, it is contemplated that the implant may be configured for introduction by a minimally-invasive surgical technique, especially percutaneous introduction, or may be configured for introduction by invasive surgery e.g. in which the site of intended implantation in the blood passage is surgically exposed from the exterior of the patient for introduction of the implant. The implant may also be percutaneously retrievable, for example a percutaneously retrievable stent, filter or frame (e.g. a spiral frame). These and other variations in the implant and its associated procedure for introduction will be apparent to those skilled in the pertinent art from the descriptions herein.

The implant structure can be made from any suitable material or combination of materials. Illustratively, the implant structure can include a metal such as stainless steel, tantalum, titanium, nitinol, cobalt, chromium, nickel, molybdenum, manganese, gold, platinum, inconel, iridium, silver, tungsten, elgiloy, alloys of any of these, or another biocompatible metal; carbon or carbon fiber; a calcium-containing inorganic material such as a ceramic; a material composed of ceramic and metallic components (cermet); or a polymeric material. The material of construction for the implant structure can be biodegradable or non-biodegradable. Nonbiodegradable polymers that can be used include for instance cellulose acetate, cellulose nitrate, silicone, polyethylene terephthalate, polyurethane, polyamide, polyester (e.g. Nylon), polyorthoester, polyanhydride, polyether sulfone, polycarbonate, polypropylene, high molecular weight polyethylene, and polytetrafluoroethylene, or mixtures of these. Biodegradable polymers that can be used include for instance polylactic acid (PLA), polyglycolic acid (PGA), poly(lactic-co-glycolic acid) (PLGA), polyanhydride, polycaprolactone, polyhydroxybutyrate valerate, or mixtures of these. Biodegradable metals may also be used, including for example biodegradable magnesium alloys.

As disclosed above, the implant is constructed so as to have the ability to localize pathogenic cells to the surface of the implant. Desirably the implant selectively localizes pathogenic cells relative to non-pathogenic cells, for example in certain embodiments selectively localizing cancer cells to the implant relative to non-cancer cells, or selectively localizing infected cells (e.g. human immunodeficiency virus (HIV) infected cells) relative to corresponding non-infected cells. In some variations, the localization of cells to the implant is effected by binding to a biological molecule or structure on the surface of the cells, such as through immunospecific or other specific binding. In this manner, using a specific binding interaction between a material of the implant and a material of the cells, specific binding to pathogenic cells and a highly selective localization of pathogenic cells on the implant, can be achieved. In other variations, a conjugate binding mechanism may be employed in which a substance (e.g. antibody or ligand) that specifically binds to the pathogenic cells in preference to non-pathogenic cells is administered systemically or locally to the patient, and in which the implant or other device is coated with or otherwise presents a binding agent (e.g. an antigen, antibody or ligand) that will immunospecifically or otherwise specifically bind to the administered substance that is in turn bound to the pathogenic cells. Suitable binding agents include, but are not limited to, a ligand or ligand analog that binds specifically to a protein, receptor, glycoprotein, carbohydrate, glycolipid, peptide, nucleic acid sequence including DNA and RNA, sugar moieties, or other cell membrane molecule or transmembrane molecule, or any combination thereof. It will be understood that even in the case of an implant configured for specific binding of pathogenic cells, it is possible that other cells may adhere and localize to the surface of the implant through other more general cellular adhesion or attachment mechanisms, although this may be minimized or essentially eliminated with a judicious selection of implant surface materials or modifications.

A variety of cancer cells may be targeted for capture on the implant. These include, for example, colorectal cancer cells, breast cancer cells, kidney cancer cells, lung cancer cells, prostate cancer cells, ovarian cancer cells, gastric cancer cells, squamous cancer cells, small-cell lung cancer cells, non-small-cell lung cancer cells, pancreatic cancer cells, testicular cancer cells, neuroblastoma cells, melanoma cells or cells from cancer of the lymphatic organs.

When used as the binding agent, an antibody can be capable of specifically or preferentially binding to a cell surface protein on the target cancer or other pathogenic cell(s) to be localized to the implant. Illustratively, antibodies or other agents that bind to the following cell surface proteins or other proteins can be used in the capture of blood borne cancer cells in accordance with certain aspects of the invention: Matrix Metalloproteinase 1 (MMP-1), associated with invasion and angiogenesis; Matrix Metalloproteinase-3 (MMP-3), associated with invasion and angiogenesis; Matrix Metalloproteinase-4 (MMP-4), associated with breast carcinoma; Matrix Metalloproteinase-5 (MMP-5), associated with invasion and angiogenesis; Matrix Metalloproteinase-9 (MMP-9), associated with invasion and angiogenesis; Matrix Metalloproteinase-11 (MMP-11), associated with breast cancer; Vascular Endothelial Growth Factor Receptor 3 (VEGFR3), associated with angiogenesis and lymphogenesis; C-C Chemokine Receptor Type 7 (CCR7), associated with gastric cancer; C-X-C Chemokine Receptor Type 5 (CXCR5), associated with neuroblastoma cells; C-X-C Chemokine Receptor Type 4 (CXCR4), associated with breast and other cancers; Neuropilin-2 (Nrp-2), associated with breast cancer, migration and invasion; Ephrin Type-A Receptor 2 (EphA2), associated with prostate cancer; Human Epidermal Growth Factor Receptor 2 (HER2), associated with breast cancer, migration and invasion (e.g. Trastuzumab or Herceptin); Cluster of Differentiation 96 (CD96) and Cluster of Differentiation 33 (CD33), associated with acute myelogenous leukemia (AML) (e.g. Gemtuzumab); and cell surface proteins associated with chronic lymphocytic leukemia (CLL) including CD20 (e.g. Rituximab or Ofatumumab), ZAP-70, CD38, CD5, CD23, CD19, CD40 (e.g. HCD122 in development at Novartis), CD45, CD45A, CD21, CD52 (e.g. Alemtuzumab); cell surface proteins associated with acute lymphoblastic leukemia including CALLA (which also may associate with chronic myelogenous leukemia, CML) and Tdt; cell surface proteins associated with lupus and/or CLL such as B-lymphocyte stimulator; Vascular Endothelial Growth Factor (VEGF) (e.g. Bevacizumab or Avastin); Epidermal Growth Factor Receptor (EGFR), associated with squamous cell carcinoma of the head and neck, colorectal carcinoma (e.g. Cetuximab and Panitumumab); Stromal cell-derived factor (SDF) protein (which binds CXCR4); Ber-EP4, associated with epithelial carcinoma; CK20, associated with breast cancer and/or colorectal cancer. Still other cell surface or other targets for metastatic cancer cells are known and can be used herein.

In preferred embodiments the implant will have antibodies or other cell binding agents adhered to the implant and available for contact with blood when the implant is deployed in a blood passage of a patient. The adherence of the antibodies or other binding agents to the implant may, for example, be through covalent or non-covalent bonding to the material of the implant structure itself or to one or more materials coated upon the implant. Alternatively, the antibody or other binding agent may be incorporated in the material of construction for the implant structure, with at least some of the incorporated antibody/binding agent available at the surface of the structure for contact with blood.

In certain embodiments the antibodies or other cell binding agents will be covalently bonded to a molecule or substance which is itself either covalently or non-covalently (e.g. with ionic, hydrogen or other non-covalent bonding interactions, or combinations thereof) bonded to the surface of the implant structure. Numerous such techniques for immobilization of antibodies to a substrate are known and can be used. In some forms, the implant structure will be made of metal, ceramic or another material that has an oxidized surface presenting oxygen or oxygen-containing functional groups, and these oxygen or oxygen-containing functional groups will be utilized to covalently, ionically, or otherwise bond or adhere the antibody or a composite molecule including the antibody to the implant surface.

For example, an antibody or other binding agent of interest can be attached to the implant surface by direct or indirect (e.g. through a linker molecule) attachment to a self assembled monolayer (SAM) of molecules attached to the implant surface. The attachment of the SAM molecules to the implant surface can be achieved by one or more of any of a variety of known methods or chemical moieties. For example, the attachment may be via one or more moieties selected from the group consisting of a thiol, a disulfide, a dithioic acid, a dithiocarbamate, a silane, a chlorosilane, a dichlorosilane, a trichlorosilane, an alkoxysilane, a dialkoxysilane, a trialkoxysilane, a hydroxyamic acid, a phosphate, a phosphonic acid, a carboxylic acid, a hydroxamic acid, an alcohol, an amine, a sulfate, a sulfonate, and a sulfinate. In some particular embodiments, the one or more self-assembled monolayer molecule is attached to the one or more surface via a phosphonic acid moiety. In many cases the SAM molecule will be an organic compound, for example having six to twenty carbon atoms, often in a straight alkyl chain.

As noted above, the attachment of the antibody or other cell binding agent to the SAM, in some embodiments, is achieved through a linker molecule, typically a polymer. Exemplary linkers include a polyethylene glycol, a dendrimer, a molecule comprising a tert-butyl protecting group, a molecule comprising an isobutylene oxide connection, an amino benzyl alcohol, a hydroxy benzyl alcohol connection, an aminobenzene dimethanol, an aminobenzene trimethanol, a hydroxybenzene dimethanol, a hydroxybenzene trimethanol, a vinyl sulfoxide, a substituted vinyl sulfoxide, a substituted methoxymethyl connection, a substituted vinyl ether connection, a carbonate connection, an ester connection, an anhydride connection, a substituted carbamic anhydride connection, a carbonic anhydride connection, an substituted urea connection, a substituted urethane connection, a substituted guanidine connection, a ether connection, a mercaptan connection, a sulfoxide connection, a sulfinate connection, a sulfonate connection, a sulfenate connection, a nitronate connection, a sulfite connection, a sulfate connection, a phosphate connection, a phosphonate connection, a phosphine connection, a silane connection, a silicate connection, a disulfide connection, a peroxide connection, an alkane connection, an alkene connection, an alkyne connection, an iodonium connection, an amino connection, a substituted allyl ether connection, a substituted benzyl ether connection and an imine connection.

The linker molecule will typically have first and second functional groups, which can be any functional groups suitable to the purposes herein. Illustrative functional groups include a hydroxyl, a carboxyl, an amino, a phosphate, a phosphonate, a sulfate, a sulfite, a sulfenate, a sulfinate, a sulfonate, a sulfoxide, a sulfone, an amide, an ester, an ketone, an aldehyde, a nitrile, an alkene, an alkyne, an ether, a thiol, a hydroxyamic acid, a silane, a silicate, a carbamodithionate, a dithionate, a mercaptan, a disulfide, a peroxide or a nitronate.

The attachment between the linker and one or more SAM molecule may be covalent or non-covalent. Similarly, the attachment between the linker and the antibody may be covalent or non-covalent.

In specific preferred embodiments, functionalized phosphonic acid compounds are used to form SAMs in which the phosphonic acid groups ionically bond with the oxygen or oxygen-containing sites at the surface of the material of the implant structure. The functional group or groups of the phosphonic acid compound can be used to bond (typically covalently) to the antibody, or to a linker molecule that is in turn bonded (again typically covalently) to the antibody.

In some forms of the invention, a pathogenic cell-specific antibody is bonded to the exterior surface of a metal implant structure with a SAM-linker-antibody structure in which the SAM is an ionically-bound SAM formed by incubating the oxidized implant surface in the presence of a functional group-containing phosphonic acid compound, and the SAM-linker structure is the reaction product of the SAM-coated implant surface with a polyethylene glycol (PEG) linker molecule having a functional group at each end, wherein at least one of the functional end groups reacts with the functional group of the phosphonic acid compound. The SAM-linker-antibody structure is then formed as the reaction product of the antibody and the SAM-linker structure by reacting the remaining functional end group of the PEG linker with an amino acid side chain or other site on the antibody. In specific embodiments, the functionalized phosphonic acid compound is mercaptododecylphosphonic acid (MDPA; also known as 12-sulfanyldodecaphosphonic acid), and the linker molecule for the reaction is maleimide-polyethyleneglycol-succinimidyl valerate (MAL-PEG-SVA), for example having a molecular weight of about 3400 Daltons. In these embodiments, the meleimide group of the MAL-PEG-SVA reacts with the sulfanyl group of the MDPA to form a covalent bond, and the remaining exposed SVA groups react with the antibody to form a covalent bond.

For additional information regarding attachment of antibodies or other molecules of interest to substrates through self assembled monolayers, reference can be made for example to United States Patent Application Publication No. 20090123516, published May 14, 2009; Adden et al., *Langmuir*, 2006 Sep. 12: 22 (19): 8197-8204; Benbenishty-Shamirt et al., *Langmuir* 2011, 27 (19): 12082-12089; and Zhang et al., *Langmuir* 2010, 26 (6): 4514-4522, each of which is hereby incorporated herein by reference in its entirety.

In other embodiments, the antibody or other pathogenic cell binding agent can be attached to the implant surface by attachment to and/or incorporation within a matrix material coated on the implant surface. Illustratively, the cell binding agent can be mixed with a matrix material, or a matrix-forming material, which is then applied to the implant surface. Alternatively, the cell binding agent can be added to a matrix material that is already coated on the implant surface, for example by applying a liquid medium containing the cell binding agent to the matrix, and then allowing the liquid to evaporate and/or otherwise causing the antibody to become stably attached to the matrix. In certain forms, the implant surface (e.g. a metal surface) can be conditioned to receive and adhere to the matrix material or matrix-forming material. For instance the surface can be treated with plasma deposition to introduce reactive chemical functionality, such as amine functionality, to the surface. A layer of matrix material or matrix-forming material can then be coated on the conditioned surface, potentially with covalent bonds formed as the product of reacting the reactive chemical functionality of the conditioned implant surface with a reactive group of the matrix or matrix-forming material. In some embodiments, amine functions of the conditioned implant surface react with carboxy functions of the matrix or matrix-forming material (e.g. a carboxy functional dextran) to form amide bonds, e.g. through water soluble carbodiimide coupling chemistry. The antibodies of other pathogenic cell-binding agents can then be covalently coupled with the matrix coating using aqueous water soluble carbodiimide chemistry in a buffered, acidic solution. For additional information regarding such matrix attachment of the antibody or other cell binding agent to the implant surface, reference can be made for example to United States Patent Application Publication No. 20070196422 published Aug. 23, 2007, which is hereby incorporated herein by reference in its entirety.

In other embodiments, the surface of the implant may be modified to have a textured or roughened surface on the nanometer or micrometer scale, herein referred to as a roughened surface. Such roughened surfaces may at least preferentially bind to circulating tumor cells relative to other circulating cells, without requiring the use of antibodies or other binding agents. For additional information regarding such roughening of implant surfaces, reference can be made for example to Chen et al., *ACS Nano*, 2013, 7(1), pp. 566-575 which is hereby incorporated by reference. Suitable surface-modification techniques for roughening include, but are not limited to reactive ion etching (RIE), chemical etching, and photolithography. Roughened surfaces may be used in combination with other surface modification or coating techniques including, but not limited to, any of the binding agents and/or associated coating techniques described herein.

The implant surface to which the antibody or other pathogenic cell-binding molecule is adhered can be nonporous or porous. Nonporous surfaces can for example be metallic or polymeric, e.g. metallic surfaces that have been subjected to electropolishing or other techniques to provide a smooth, nonporous surface.

Porous implant surfaces will be used in certain embodiments, and when used can serve to provide an increased surface area for cell capture as compared to a corresponding smooth surface. Porous surfaces can be provided, for example, by manufacturing the implant structure from a porous material so as to present a porous surface to the implant. Porous implant surfaces can also be provided, for example, by coating a porous material onto a surface of an implant structure that is nonporous or less porous than the applied porous material. Such a coated porous material can comprise an organic material, and inorganic material, or a combination thereof. Organic materials include polymers, which can be coated as porous materials or modified after coating to provide porosity. Suitable polymers include for example any of those polymers discussed elsewhere herein. Inorganic material coatings can for instance be porous metal or porous glass or ceramic coatings. The porous metal coating can include a metal or metal alloy from among those metals identified elsewhere herein. Porous ceramic coatings include for example porous calcium-phosphate containing coatings.

In this regard, a calcium phosphate coating may be deposited on the implant surface by any suitable method. In certain forms, the coating is deposited by an electrochemical deposition (ECD), an electrophoretic deposition (EPD), a sol gel (SG), an aero-sol gel (ASG), or a biomimetic (BM) process. These processes can be varied to achieve the desired porosity and/or coating thickness features. In certain embodiments, the calcium phosphate coating can be thin, for example having a thickness of no more than 5 µm, such as a thickness of no more than 2 µm. Additionally or alternatively, the calcium phosphate in the coating can have a porosity volume ranging from 30 to 70% and/or an average pore diameter ranging from about 0.1 µm to about 100 µm, or from about 0.1 µm to about 10 µm. Calcium phosphates displaying various combinations of the disclosed thicknesses, porosity volumes or average pore diameters can also be prepared. As well, the calcium phosphate of the coating can comprise at least one calcium phosphate selected from hydroxyapatite, octacalcium phosphate, alpha-tricalcium phosphate, beta-tricalcium phosphate, amorphous calcium phosphate, dicalcium phosphate, calcium deficient hydroxyapatite, and tetracalcium phosphate. The coating can comprise a pure phase of any of these calcium phosphates or mixtures thereof. In some embodiments, the calcium phosphate can be essentially pure hydroxyapatite, or can be a mixed-phase coating comprising partially crystalline hydroxyapatite and dicalcium phosphate dihydrate. For additional information regarding the formation of porous coatings onto implant surfaces, reference can be made to U.S. Patent Application Publications 20100217377 published Aug. 26, 2010 and 20060134160 published Jun. 22, 2006, both of which are hereby incorporated by reference in their entirety.

When a porous surface is provided for adherence of the pathogenic cell binding agent, the agent can be adhered to the surface by any suitable method. For instance, methods disclosed hereinabove can be used. In certain embodiments, a porous calcium phosphate surface is provided and the binding agent is attached either directly or through a surface functionalized with an organic reagent such as an organosilane compound. Using these methodologies, known reactive functional groups such as hydroxyl, carboxyl, amino, phosphate, phosphonate, sulfate, sulfite, sulfenate, sulfinate, sulfonate, sulfoxide, sulfone, amide, ester, ketone, aldehyde, nitrile, alkene, alkyne, ether, thiol, hydroxyamic acid, silane, silicate, carbamodithionate, dithionate, mercaptan, disulfide, peroxide or nitronate groups can be used to couple (including covalently couple) the antibody or other cell binding agent to the porous surface, either directly or through a linker molecule such as a polyethylene glycol linker. For additional information regarding antibody immobilization on solid inorganic surfaces, reference can be made for example to Weetall et al., *Applied Biochemistry and Biotechnology*, Vol. 22, 1989, pp. 311-330, which is hereby incorporated herein in its entirety.

The coating with the antibody or other pathogenic cell-binding agent can be present on the entire surface of the implant, or on only a portion of the surface of the implant. In some embodiments, such coating is present at least on a portion of the implant that extends into the lumen of the vascular passage when the implant is stably deployed in the passage. For example, a portion of the implant that extends transversely to and inwardly from the wall of the vascular passage can be coated with the antibody or other pathogenic cell binding agent. Illustratively, when the implant is a vascular filter having elongate legs with portions that contact the vessel wall when implanted and portions that extend inwardly from the vessel wall when implanted so as to be suspended in the passage and not in contact with the vessel wall, at least those portions that do not contact the vessel wall can be coated with the antibody or other pathogenic cell-binding agent; and, in certain embodiments, only portions of the filter or other implant which are suspended within the lumen of the passage (not in contact with the vessel wall) will be coated with the antibody or other pathogenic cell binding agent. In these embodiments, the lumen-suspended implant portions can be coated completely circumferentially with the antibody or other pathogenic cell binding agent, while nonetheless avoiding positioning of the suspended coating material against the vessel wall.

The implant can be coated with one or more other active agents in addition to the antibody or other pathogenic cell binding agent. This other active agent(s) can be incorporated in the same coating or in one or more different coatings than the pathogenic cell binding agent, potentially at locations on the implant that are spaced from the pathogenic cell binding agent. Illustratively, such one or more active agents can include the following agents alone or in combination: chemotherapeutic agents, radiation sensitizing agents, radioprotective agents, anti-restenosis agents (e.g. sirolimus, paclitaxel, tacrolimus, pimecrolimus, everolimus, or derivatives or analogs of any of these), anti-inflammatory agents, antiproliferative agents, pro-healing agents, gene therapy agents, extracellular matrix modulators, anti-thrombotic agents/anti-platelet agents, antiangioplastic agents, antisense agents, anticoagulants, antibiotics, bone morphogenetic proteins, integrins (peptides), disintegrins (peptides and proteins), smooth muscle cell inhibitors, antioxidants, immunosuppressive agents, and anti-antigenic agents. In certain embodiments, the implant will be coated with a radiation sensitizing agent that elutes from the implant so as to contact and sensitize cancer or other pathogenic cells captured by the implant to destruction by radiation. Radiation sensitizing agents for these purposes may include, as examples, metoclopramide, sensamide, neusensamide, profiromycin, RSR13 (2-[4-[[(3,5-dimethylanilino)carbonyl]methyl]phenoxyl]-2-methylpropionic acid), etanidazole, lobenguane, gadolinium texaphrin, BuDR/Broxine, IPdR (5-iodo-2-pyrimidinone-2'-deoxyribose), CR2412, L1X, agents that reduce hypoxia, and others. In addition or alternatively, the implant can be coated with a radioprotective agent that elutes into surrounding tissue when the implant is implanted, for example to protect that tissue during radiation applied to the implant to destroy captured cancerous or other pathogenic cells. In certain embodiments the implant can have a coating comprising a radioprotective agent at least on portions of the implant that contact the vessel or other passage wall when the implant is stably implanted, and such coating can elute the radioprotective agent to the wall tissue to provide protection to that wall tissue during radiation applied to the implant. Illustrative radioprotective agents for these purposes include for example antioxidants, free radical scavengers, cytokines, flagellin and latent TGF-beta. Antioxidants and free radical scavengers that may be used include for instance thiols, such as cysteine, cysteamine, epigallocatechin gallate, glutathione and bilirubin; amifostine (WR-2721); vitamin A; vitamin C; vitamin E; tempol; melatonin; and flavonoids such as Indian holy basil (*Ocimum sanctum*), orientin and vicenin. Cytokines and growth factors can confer radioprotection by replenishing and/or protecting the radiosensitive stem cell populations. Cytokines that may be used as radioprotective agents include stem cell factor (SCF, c-kit ligand), Flt-3 ligand, interleukin-1 fragment IL-1 b-rd, and keratinocyte growth factor (KGF). Other factors that stimulate the proliferation of immunocytes may also be used. These include, 5-AED (5-androstenediol), and synthetic compounds, such as ammonium tri-chloro(dioxoethylene-O,O'-)tellurate (AS-101). When used, in some inventive variants, a radioprotective agent will be provided on the implant only on a portion or portions spaced from the pathogenic cell binding agent, so as to prevent or minimize any protective activity of the agent on the pathogenic cells intended for destruction.

Generally, in use, the implant can be introduced into a blood passage of a patient, and implanted there either temporarily or permanently. The implant captures cancer or other pathogenic cells circulating with blood of the patient via the binding agent, and thereby localizes the cells at or near the implant surface. After a period of implantation sufficient to localize the target pathogenic cells, the cells can be eliminated. This may occur, for example, by removal of the implant along with the pathogenic cells, or by destruction (killing) of the pathogenic cells. For these purposes, the cells can be destroyed by any suitable means. These include destruction by radiation, chemotherapeutic agents, heat, or other conditions, or combinations thereof, which preferentially destroy the pathogenic cells relative to non-pathogenic cells of the patient. After the destruction of the localized pathogenic cells, the implant can be left implanted, potentially to repeat the pathogenic cell localization/destruction cycle, or can be removed. The application of the cell-destroying agent can be systemic or localized in the patient, and can be applied from an external source (e.g. external radiation focused on the implant), or applied internally, for example by catheterization to locally administer a chemotherapeutic agent to the region of the implant and/or to locally administer radiation to the region of the implant. In one mode, local chemotherapeutic agent administration can be achieved by isolating the segment of the vascular vessel in which the implant resides between two inflatable balloons (e.g. longitudinally spaced on a dual balloon catheter), and administering a liquid chemotherapeutic agent into the isolated segment to destroy the cancer or other pathogenic cells localized to the implant. Part or essentially the entire amount of the administered chemotherapeutic agent can then optionally be withdrawn from the isolated segment by catheter so as to avoid or reduce the amount of systemic release of the chemotherapeutic agent when the balloons are deflated and removed.

The implant can be introduced into the cardiovascular system of a patient at any suitable location. Illustratively, in certain embodiments, the implant is introduced in a location spaced from a tumor or other cancerous mass of tissue (e.g. cancerous organ) in the patient, for example by introduction in the central vascular system, e.g. in the inferior vena cava. Nonetheless, cancer cells that migrate from the tumor or other cancerous mass into the bloodstream can travel to the implant for capture and potential destruction or removal. In other embodiments, the implant is introduced in a vascular passage proximate to a tumor or cancerous organ or other mass, for example immediately downstream therefrom, in order to capture potential metastasizing cancer cells soon after they enter the blood stream. In still other embodiments, the implant is introduced immediately upstream of an organ or other tissue region to be protected from blood-borne, potential metastasizing cancer cells, in order to capture the blood-borne cancer cells before they enter the organ or other protected tissue region. It will also be understood that multiple implants can be used, in combinations of any of these pathogenic cell-capture strategies, and that upon the removal of an implant, another pathogenic cell-capturing implant (e.g. another of the same implant) can be introduced for further treatment.

In the practice of aspects of the invention, the pathogenic cell binding agent on the implant can be specific to a single type of pathogenic cell, or can effectively bind multiple different types of pathogenic cells. In either case, the cell binding agent desirably binds only to the pathogenic cell(s) or at least preferentially binds the pathogenic cell(s) relative to non-pathogenic cells of the patient. Utilization of a cell binding agent capable of specific or preferential binding to multiple different types of pathogenic cells relative to non-pathogenic cells is beneficial because it increases the robustness of use of a particular implant, in that the same implant design can be used in patients with differing pathogenic cell diseases. A mixture of several different binding agents, each with a differing target pathogenic cell population, can also be used to provide enhanced robustness of use for a given implant.

Figure 1:
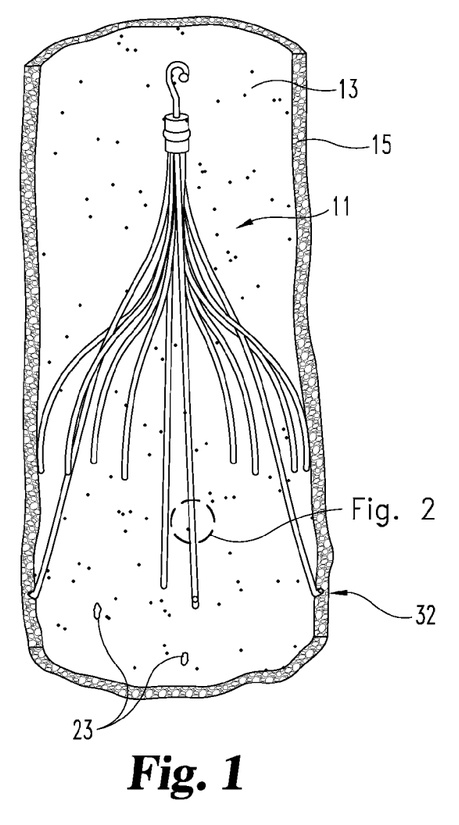
FIG. 1 is a partial cross-sectional view of a blood vessel lumen containing an implantable filter with a coating for cancer cell capture.

The following disclosure refers to a number of Figures in describing embodiments of implants which can be placed within the vasculature of a mammal and have a surface that captures blood-borne cancer cells. It will be understood that any and all of the features discussed hereinabove with respect to the components, manufacture, and operation of implants of the invention can apply to the depicted embodiments, unless indicated otherwise. Referring now to FIG. 1, shown is one embodiment of an implant 11 placed within blood vessel lumen 13 having blood-borne cancer cells or other pathogenic cells 23 flowing therein. Implant 11 includes a surface coating 22 that is configured to bind to blood-borne pathogenic cell 23 at the location of implant 11, as shown in FIG. 2.

Figure 2:
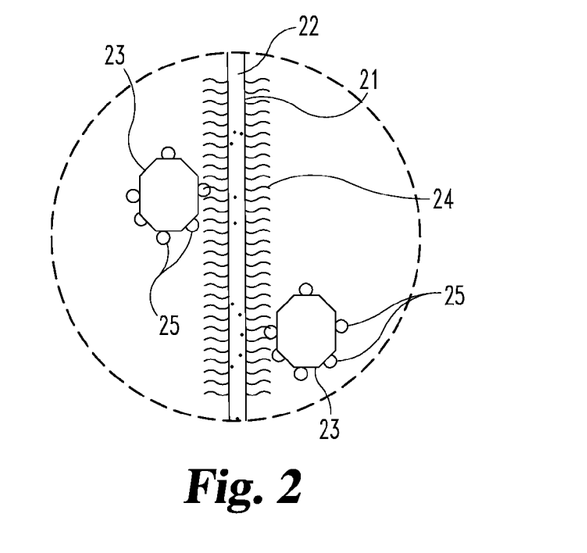
FIG. 2 is an enlarged view of a portion of the cancer cell collector of FIG. 1.

Surface coating 22 includes cancer or other pathogenic cell specific binding agents 21, as shown in FIG. 2. In FIG.

2, binding agents 21 can be in the form of linker-attached antibodies 24 which project outward from the surface of implant 11. Antibodies 24 can specifically bind to cell surface receptors or other proteins 25 on targeted blood-borne pathogenic cells 23.

Implant 11 with surface coating 22 is placed in the vasculature to expose collector 11 to flowing blood, allowing binding agents 21 to bind to cell surface receptors or other proteins 25 on cells carried in the bloodstream so that circulating targeted blood-borne pathogenic cells 23 are localized on implant 11 as shown in FIG. 2. This collects blood-borne pathogenic cells 23 on implant 11 within blood vessel lumen 13, and prevents such cells 23 from traveling to other parts of the body, thus potentially reducing or preventing new tumor sites.

Surface coating 22 can be applied to the surface of implant 11 by any known method. For example, coating 22 (and binding agents 21) can be applied by dipping, spraying, or any other suitable means of application, e.g. as discussed hereinabove. Surface coating 22 can be selectively applied to any desired surface on implant 11, such as surfaces expected to come into contact with blood flow when implant 11 is placed within the vasculature of the patient.

Figure 3:
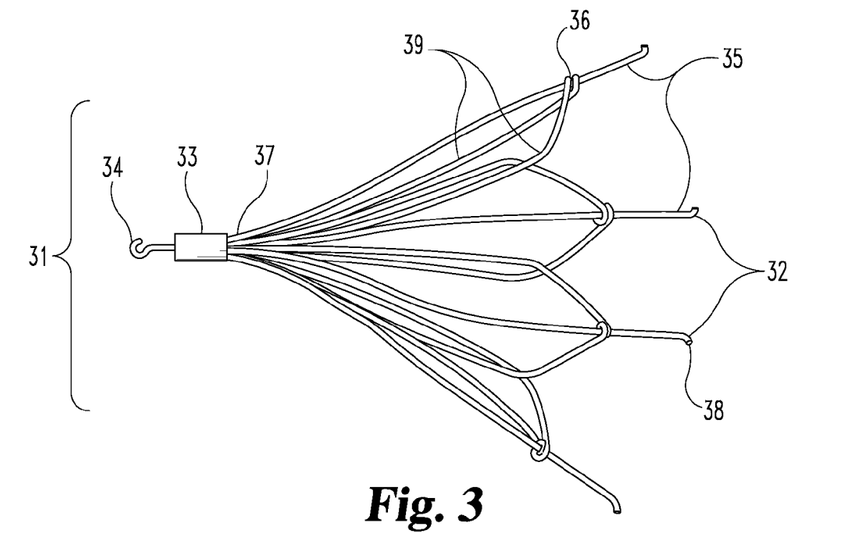
FIG. 3 is a perspective view of a vena cava filter with a coating for cancer cell capture.
Figure 4:
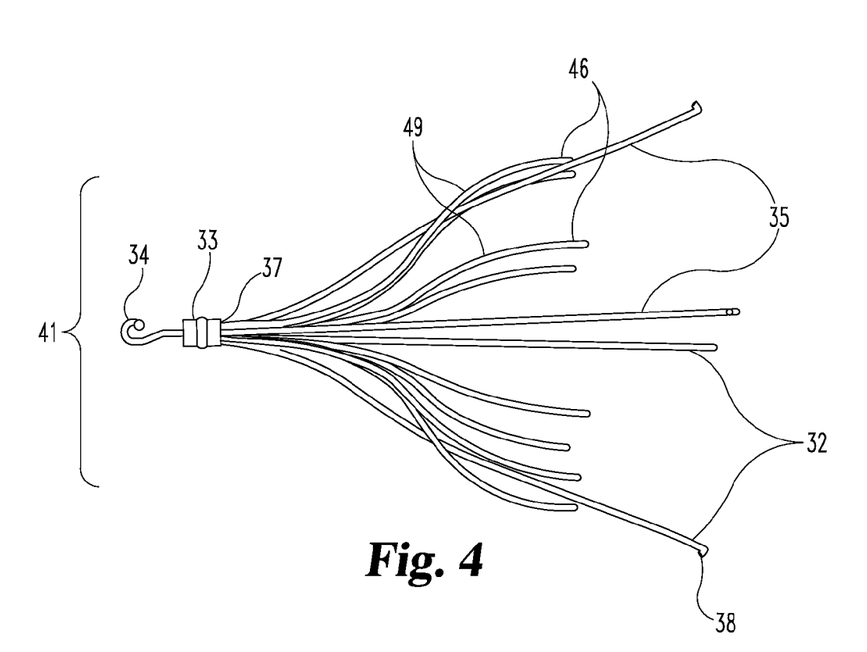
FIG. 4 is a perspective view of an alternate embodiment of a vena cava filter with a coating for cancer cell capture.

Referring now to FIGS. 3 and 4, illustrated are vena cava filters 31 and 41, two possible embodiments of implants 11. Filters 31 and 41 include hub body 33 and a plurality of primary struts 35 that divergingly extend distally from hub body 33. Primary struts 35 have proximal ends 37 that are secured to hub body 33. Primary struts 35 include distal end portions that terminate at anchoring hooks 32. The proximal end of hub body 33 includes hook 34 that extends opposite of primary struts 35. Primary struts 35 are configured to be biased into a collapsed state where collector 11 fits within a delivery device, such as a catheter, for placement and retrieval from the vasculature. When extracted from the delivery device and positioned in the vasculature, primary struts 35 provide a biased force that embed anchoring hooks 32 in the vessel wall to secure the position of implant 11 as shown in FIG. 1.

Referring to FIG. 3, filter 31 includes a plurality of secondary struts 39 that divergingly extend distally from hub body 33. Secondary struts 39 have proximal ends 37 that are secured to hub body 33 and distal ends 36 that are slidingly connected to primary struts 35.

Referring to FIG. 4, filter 41 includes a plurality of secondary struts 49 that divergingly extend distally from hub body 33. Secondary struts 49 have proximal ends 37 that are secured to hub body 33 and distal ends 46 that divergingly extend generally axially from hub body 33.

Primary struts 35 of filters 31 and 41 are spring biased such that when in a deployed position, anchoring hooks 32 engage blood vessel interior wall 15, as shown in FIG. 1. Anchoring hooks 32 include barbs 38 that project generally axially toward hub body 33. In conjunction with spring biasing provided by struts 35, barbs 38 function to retain filters 31 and 41 at the location of deployment as barbs 38 anchor filters 31 and 41 to interior wall 15 of blood vessel lumen 13, as shown in FIG. 1. Filters 31 and 41 are deployed in blood vessel lumen 13 with hub body 33 being downstream of anchoring hooks 32 such that the pressure from the blood flow on filters 31 and 41 contributes to maintaining barbs 38 anchored in interior wall 15. Inserted into the vasculature in this way, filters 31 and 41 are situated in blood vessel lumen 13 so that blood flowing through blood vessel lumen 13 and carrying blood-borne cancer or other pathogenic cells 23 passes through filters 31 and 41.

Figure 6:
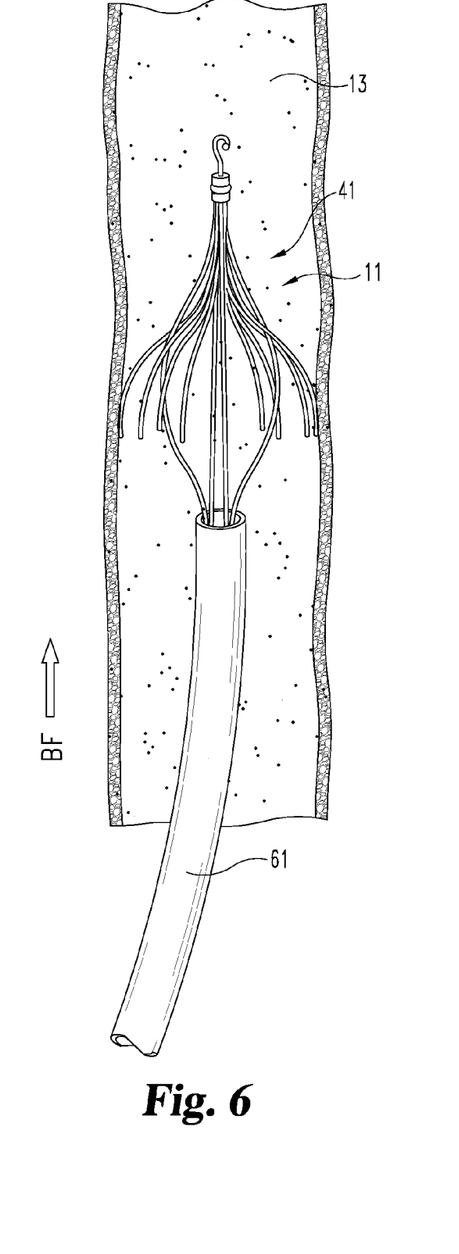
FIG. 6 is a partial cross-sectional view of a blood vessel lumen illustrating the insertion of the FIG. 4 coated vena cava filter using a catheter.

Referring now to FIG. 6, filter 41 is illustrated being deployed from catheter 61. While implant 11 can be located anywhere in the vasculature of a mammal, the embodiment shown in FIG. 6 can be deployed to and retrieved from the inferior vena cava through the jugular vein or femoral vein. While not illustrated, filter 41 is initially collapsible such that filter 41 is substantially contained within catheter 61, permitting catheter 61 to be inserted in the vasculature and moved to a deployment location where filter 41 can then be deployed through catheter 61 as known in the art.

Filter 41 is also operable to be re-collapsed and removed using a similar procedure. Retrieval of filters 31 and 41 can be achieved by a catheter and retrieval device that snares hook 34 and pulls filter 31 or 41 into a retrieval device such as a catheter thereby collapsing struts 35 and 39 or 49 into the retrieval device and disengaging hooks 32 from interior wall 15. The retrieval device can then be removed from the vasculature of the mammal along with filter 31 or 41.

The distal end sections of primary struts 35 can include a bioactive material, such as an antiproliferative or anti-inflammatory agent configured to inhibit or prevent the ingrowth of tissue to and around the distal end portions and anchoring hooks 32, at least for an extended length of time after placement, thereby substantially extending length of time that filter 31 or 41 can be safely left in the vasculature prior to retrieval.

Figure 5:
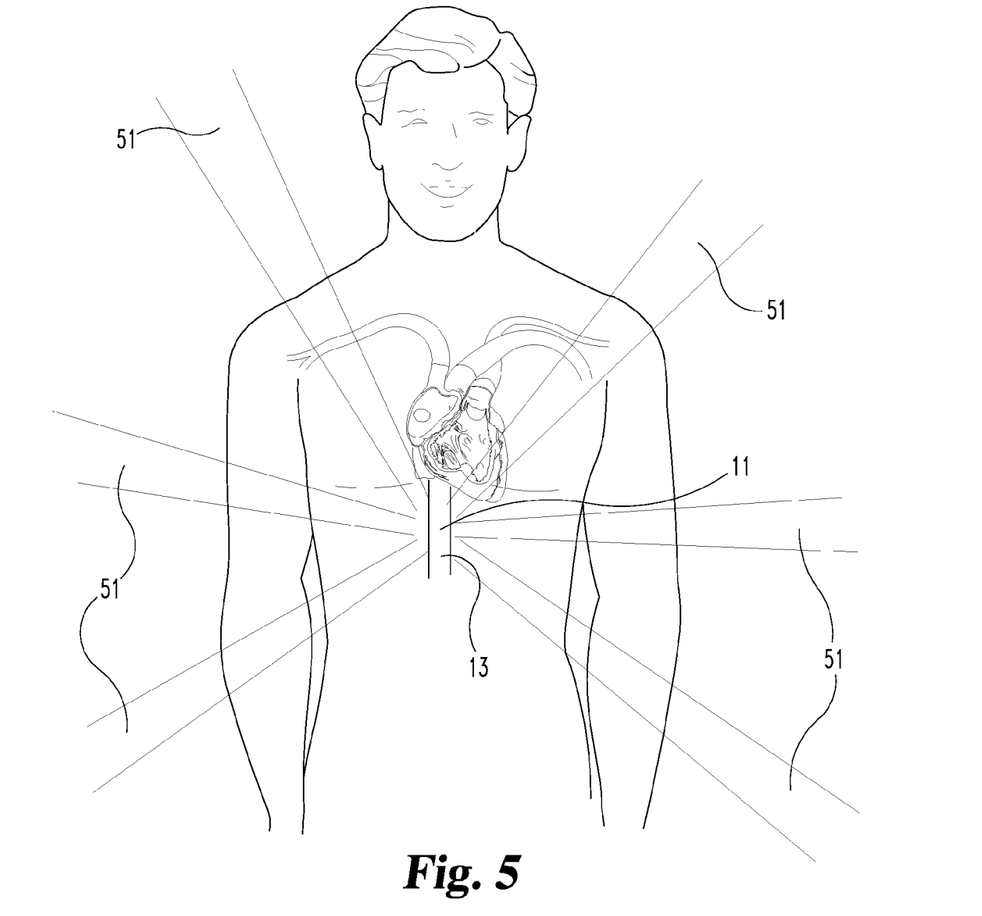
FIG. 5 is a partial cross-sectional view of a patient including a cancer cell collecting filter implanted in the vasculature illustrating radiation therapy targeted at the filter.

Implant 11 can be placed in blood vessel lumen 13 and left for any period of time sufficient for blood-borne pathogenic cells 23 to become captured at the location of implant 11. Collected cells 23 that are captured at implant 11 can be either removed or eradicated by any suitable means. For example, standard oncology techniques including radiation therapy can be narrowly targeted at implant 11, as shown in FIG. 5, to eradicate collected cancer cells 23. Techniques for applying targeted radiation to destroy living cancer cells in a selected region are well known in the art and can be used herein.

For example, as shown in FIG. 5, radiation fields 51 can be narrowly focused at the location of implant 11. It may be necessary to include a margin of normal tissue around implant 11 to allow for uncertainties in set-up and patient structure movement. These uncertainties can be caused by internal movement (for example, respiration and bladder filling) and movement of external skin marks relative to the tumor position. To spare normal tissues (such as skin or organs which radiation must pass through in order to treat the tumor), shaped radiation beams can be aimed from several angles of exposure to intersect at implant 11, providing a much larger absorbed dose at implant 11 than in the surrounding tissue.

Implant 11 may optionally incorporate a radiopaque material such as derivatives of tungsten, barium, bismuth, etc. Such material would not allow X-rays or similar radiation to pass. The radiopaque material could be used to provide enhanced x-ray response and improved locating precision of collector 11, thereby reducing uncertainties in radiation accuracy. Implant 11 may also optionally incorporate one or more echogenic features for visualization of the implant using external ultrasound or intravascular ultrasound (IVUS) techniques.

Another way to eliminate pathogenic cells 23 from the body of the patient is to physically remove them. After placement for a period of time sufficient to immobilize blood-borne pathogenic cells 23 at the location of implant 11, implant 11 may be removed from the vasculature along with the immobilized pathogenic cells 23. Optionally, implant 11 can then be purged of all immobilized cancer cells 23 by any suitable means such as, for example, sterilization or radiation, and purged implant 11 can then be placed back into blood vessel lumen 13 to begin the collection process again; alternatively, a new implant 11 can then be placed into blood vessel lumen 13 to begin the collection process again. Implant 11 could also be removed from blood vessel lumen 13 along with all immobilized pathogenic cells 23 and discarded, with the optional collection and retention of a sample of the pathogenic cells 23 for diagnostic or other study purposes.

Figure 7:
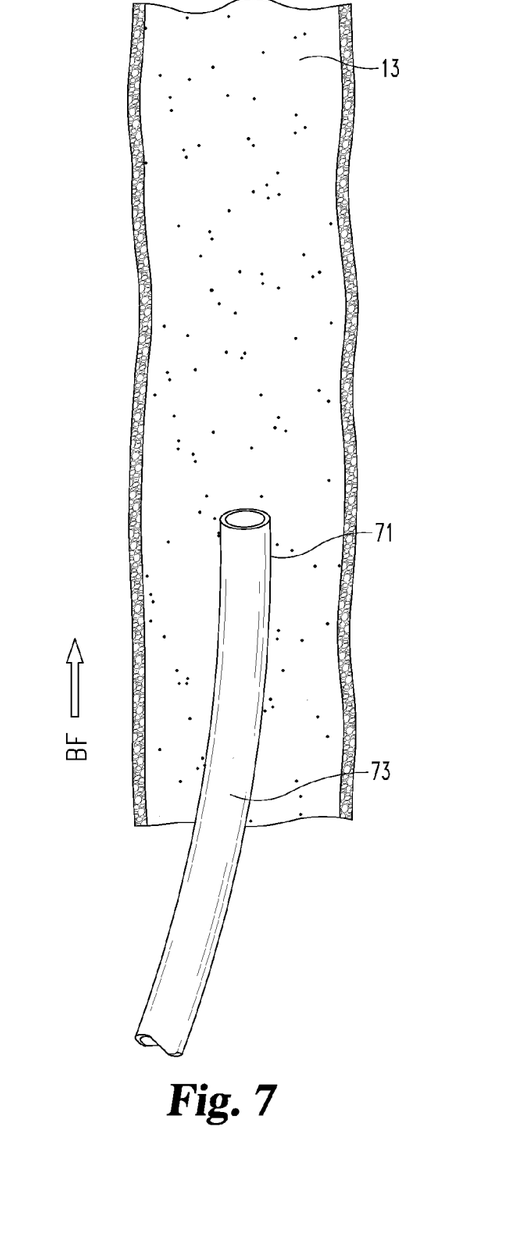
FIG. 7 is a partial cross-sectional view of a blood vessel lumen containing an alternate embodiment of a cancer cell collecting implant.

FIG. 7 illustrates catheter 71, another alternative embodiment of implant 11, that is placed within blood vessel lumen 13 and has surface coating 73 that includes pathogenic cell specific binding agents as discussed above. Often catheters are placed within the vasculature of a cancer patient for extended periods of time. Surface coating, as described above, can be applied to other types of objects placed within a blood vessel, such as catheter 71. Catheter 71 can be any type of catheter that is normally placed for more than mere temporary duration and which are commonly placed in cancer patients or other patients having blood-borne pathogenic cells, including peripherally inserted central catheters, central venous catheters, Hickman lines, Groshong lines, and balloon catheters, including perfusion balloon catheters. In this way, catheter 71 is situated in blood vessel lumen 13 such that blood flowing through blood vessel lumen 13 and carrying cancer cells 23 passes over surface coating 73 including pathogenic cell specific binding agents as discussed above.

Figure 8:
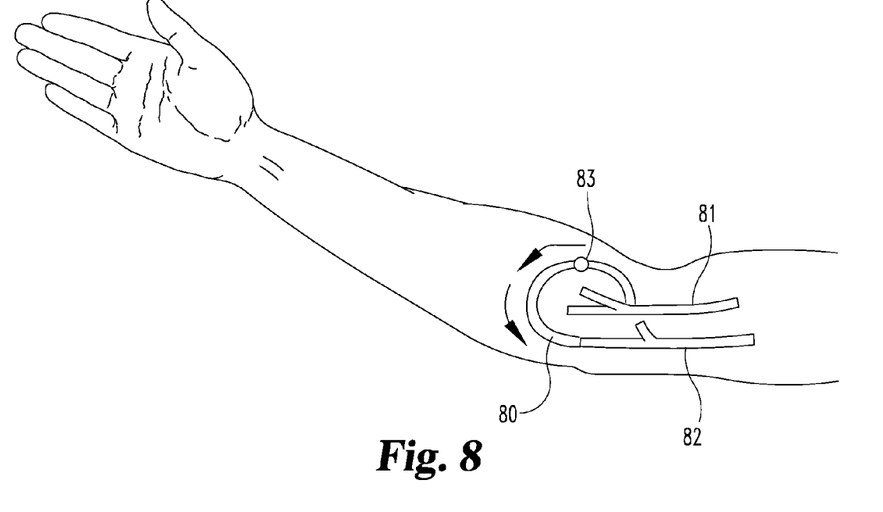
FIG. 8 is a perspective view of one illustrative embodiment of an extracorporeal blood flow circuit incorporating a pathogenic cell capture device.

FIG. 8 provides an illustration of an extracorporeal blood flow arrangement that can be utilized in accordance with one embodiment of the invention. An artificial tubular device 80 such as a catheter, graft or shunt connects an artery 81 to a vein 82 of the patient to establish a flow of blood (see arrows) in the device 80 in which blood is passed from artery 81, through device 80 and into vein 82. In other arrangements, a graft, shunt or other tubular member can be used in defining an extracorporeal blood circuit that connects an artery to an artery, or a vein to a vein. In any of these arrangements, an extracorporeal blood pump may also optionally be utilized. A pathogenic cell-capturing device or device portion 83 is provided in contact with the flow of blood through device 80. An implant device such as any of those described herein can be used as a cell-capturing device 83, positioned within tubular device 80, and/or the cell-capturing device may be another device such as a membrane through which blood is passed (e.g. a dialysis membrane). Alternatively, or additionally, an inner lumen surface of tubular device 80 can present a pathogenic cell binding agent such as any of those described herein, for example by being coated with the pathogenic cell binding agent. Pathogenic cells such as cancer or other cells identified herein will be captured and localized to device or device portion 83, and thus removed from the natural blood flow circuit of the patient. In one mode of operation, this simple physical removal can be sufficient for pathogenic cell capture and processing to benefit the patient, with the potential option of replacing tubular device 80 and/or device or device portion 83 when the pathogenic cell binding capacity thereof has become exhausted. In another mode of operation, pathogenic cells captured by device or device portion 83 can be destroyed, for example using radiation or any other agent described herein or otherwise suitable, continuously or intermittently during treatment of the patient with the cell-capturing extracorporeal circuit. These and other suitable modes of operation will be apparent to the skilled person from the descriptions herein.

For the purpose of promoting a further understanding of aspects of the present invention, the following specific examples are provided. It will be understood that these examples are illustrative, and not limiting in nature.

EXAMPLE 1

Surface Modification of Implantable Devices

Elgiloy sheet (cobalt-chromium-nickel alloy) was purchased from Elgiloy Specialty Metals (Elgin, Ill.) and wafers measuring 0.5 inches by 1 inch or 1 inch by 3 inches were cut from the sheet. These wafers were washed with detergent and a brush to remove any surface dirt and were then rinsed with water and dried. An oxide layer was then deposited on the surface of the wafers by electropolishing. The wafers were then hung vertically in a solution of 12-mercaptododecylphosphonic acid in dry tetrahydrofuran (approximately 8 mg 12-mercaptododecylphosphonic acid in approximately 30 mL dry THF) and the solvent was allowed to slowly evaporate. The wafers were then warmed in an oven at 120° C. for 63 hours. Upon removal from the oven, the wafers were washed in a THF bath and sonicated for 20 minutes, removed from the THF bath, and any residual THF was removed by evaporation. The wafers were placed horizontally in a petri dish and a solution of Maleimide-polyethyleneglycol(PEG)-succinimidyl valerate(SVA) in water at pH 7.5 was added so that solution covered the surface of the wafer but did not spread beyond the wafer (Laysan, Catalog No.: MAL-PEG-SVA-3400-100 mg, molecular weight: 3400 Da, Lot No.: 123-141, approximately 3 mg/mL). The solution was left to stand for 4 hours. After 4 hours, the wafers were rinsed with Millipore purified water and dried with a stream of $N_2$. A solution of anti-epidermal growth factor receptor ($\alpha$-EGFR) was prepared by dissolving $\alpha$-EGFR (Santa Cruz Biotechnology, EGFR(N-20)sc-31155, goat anti-human, anti-mouse, anti-rat, stored at 4° C., stock solution of 200 µg in 1 mL phosphate buffered saline (PBS) with >0.1% sodium azide and 0.2% gelatin) in water at 4° C. and pH 8.5. The wafers were submerged in the solution of $\alpha$-EGFR and allowed to stand overnight at 4° C. with gentle shaking. The wafers were then removed from the $\alpha$-EGFR solution and were washed eight times with 0.125 M sodium tetraborate buffer solution at pH 10 containing 0.066% (w/v) sodium dodecyl sulfate (SDS). The wafers were then washed once with phosphate buffered saline (PBS) and were dried under a stream of $N_2$.

The wafers were sterilized by placing the wafers in a plastic holder. The wafers and plastic holder were then placed in a Kevlar pouch. This assembly was sterilized by low-temperature ethylene oxide (EtO) sterilization. After sterilization the wafers were aerated for at least 24 h before use.

It will be understood that medical implants, including those identified in the present disclosure, can be coated using procedures generally as discussed above for the wafers, adapted to the particular implant material or geometry as necessary. Illustratively, an elgiloy vena cava filter can be thus coated. As well, other binding agents can be used in the place of the $\alpha$-EGFR.

EXAMPLE 2

Parallel Plate Flow Testing

Wafers as prepared in EXAMPLE 1 were tested for durability against shear flow. The wafer to be tested was placed as the slide for a Glycotech (Gaithersburg, Md.) flow chamber with a rubber gasket between the wafer and flow chamber. The chamber was sealed. A syringe pump was connected to the flow chamber inlet and the outlet of the flow chamber ran into a beaker. PBS at 37° C. was pumped through the system at a rate of 1.25 mL for 30 minutes. This rate was chosen to place approximately 1.5 dyne/cm$^2$ of stress on the surface of the wafer to estimate the physiological stress level in the vena cava. After 30 minutes the wafer was removed from the flow chamber and stained to assess the durability of the surface modification.

EXAMPLE 3

Staining of Modified Surface

The extent of surface modification was estimated by staining the modified surface to visualize the extent of modification. Approximately 1 mL of a solution containing 10% mouse serum (Pierce ThermoScientific, Product No.: 31881) in diluted tris buffered saline (TBS, Santa Cruz Biotechnology, sc-362188) was prepared and transferred by pipette onto the surface of a 1 inch by 3 inch wafer. The wafer and serum solution were incubated at 37° C. in a humidified chamber overnight. The next day, the serum solution was decanted from the wafer.

Cold mouse anti-goat IgG-HRP antibody (Santa Cruz Biotechnology, sc-2345) was diluted in a fresh solution of 10% porcine serum in TBS at a 1:20 ratio of antibody to solution ratio (v/v) and was kept chilled. Approximately 250 µL of this solution was transferred by pipette onto the surface of the wafer and was incubated at 37° C. in a humidified chamber overnight.

The next day, the wafer was washed three times for five minutes on a rocker plate with TBS by submerging the wafers in a TBS solution in a petri dish using fresh TBS solution for each wash.

A dilute solution of 3,3'-diaminobenzidine (DAB, CAS No.: 91-95-2) was used to visualize the cells on the wafer surface. A solution of TBS in 3% hydrogen peroxide (100:1 TBS:H$_2$O$_2$ v/v) was prepared and DAB was diluted with this solution in a ratio of 1:50 v/v DAB to TBS/H$_2$O$_2$. Approximately 1 mL of the resulting dilute solution of DAB was then transferred by pipette onto the surface of the wafer. A brown color then appeared and the wafer was rinsed twice with TBS. A photograph of the wafer was obtained and the amount of surface modification was quantified. The data suggest that the coating is at least minimally durable under flow conditions.

EXAMPLE 4

Cell Adhesion to Modified Surface—Static Model

A wafer with modified surface as prepared in the Examples above was placed in a sterile dish. A solution of SW480 Human epithelial colorectal adenocarcinoma cells (EGFR+, ATCC CCL-228, approximately 10 cells/mL) was added to completely submerge the wafer. The wafer was allowed to rest in the solution for approximately 4 hours. The wafer was then removed from the dish, the surface of the wafer was washed free of non-adherent cells with PBS and stained according to the above protocol. Visual inspection of the stained wafer surface revealed cells adhered to the surface of the wafer.

EXAMPLE 5

Cell Adhesion to Modified Surface—Flow Model

A wafer with modified surface as prepared in the Examples above was placed in a parallel plate flow apparatus with the wafer used as the bottom slide. The chamber was sealed. A syringe pump was connected to the flow chamber inlet and the outlet of the flow chamber ran into a beaker. A solution of SW480 Human epithelial colorectal adenocarcinoma cells (EGFR+, ATCC CCL-228, approximately 10 cells/mL) were pumped through the chamber at a rate of approximately 1.26 mL/min. After 30 min the flow through the apparatus was stopped, the wafer removed from the apparatus and the surface was washed free of non-adherent cells with PBS and the surface stained according to the above protocol. Visual inspection of the stained wafer surface revealed cells adhered to the surface of the wafer.

EXAMPLE 6

Cell Adhesion to Modified Surface—Flow Model II

The following test wafers are prepared: (a) an unmodified wafer; (b) a surface modified wafer with αEGFR antibody that is sterilized; (c) a surface modified wafer with αEGFR antibody that is not sterilized; (d) a surface modified wafer where half the surface is modified with αEGFR antibody and where half the surface is not modified that is sterilized; (e) a surface modified wafer where half the surface is modified with αEGFR antibody and where half the surface is not modified that is not sterilized; (f) a wafer with a surface modified by a nanoroughening procedure; (g) a wafer with a surface modified by a nanoroughening procedure and with the presence of αEGFR antibody on the nanoroughened surface; and (h) a surface modified wafer with BSA antibody. The surface-modified wafers are each placed in a parallel plate flow chamber with the wafer as the bottom side and the chamber is sealed. A cellular suspension medium is prepared for use in the parallel flow apparatus with a cell concentration of approximately 10 cells/mL. The cellular suspension medium is passed through the chamber at a flow rate of 1.26 mL/min using a syringe pump. The cellular suspension medium is allowed to pump through the parallel plate flow chamber for 30 minutes to 2 hours. Thereafter, the flow is stopped, and the wafer is removed from flow chamber and gently rinsed with phosphate buffered saline to remove non-adherent cells from the surface of the wafer. The wafer surface is stained as described in the Examples above to visualize cells adhered to the wafer surface. Alternatively, the cells may be stained as follows: The surface of the wafer is rinsed with distilled water. A solution of hematoxylin (Santa Cruz Biotechnology, sc-24973, Gill's II formulation) is contacted with the surface of the wafer and allowed to stand for two minutes. The surface of the wafer is then rinsed with distilled water for two minutes. 0.5 mL of bluing reagent (ammonia solution 0.084% w/v NH$_4$OH in H$_2$O) are added to the surface of the wafer and allowed to stand for 30 seconds. The surface of the wafer is rinsed with distilled water for 3 minutes. A solution of Eosin Y (Santa Cruz Biotechnology, sc-203734, 1% w/v in EtOH and 0.5% acetic acid) is then contacted with the wafer surface and allowed to stand for two minutes. The surface of the wafer is then rinsed again with distilled water for 3 minutes. Cells are then observed on the surface of the wafer with a microscope and the extent of cellular adhesion is assessed. Similar tests can be conducted using other binding agents, including those binding agents identified in the present disclosure.

Although preferred embodiments and the best mode of the invention have been described in the foregoing description, it will be understood that the invention is not limited to the specific embodiments disclosed herein but is capable of numerous modifications by one having ordinary skill in the art. It will be understood that the material used and the pharmaceutical details may be slightly different or modified from the description herein without departing from the methods and compositions disclosed and taught by the present invention.

This disclosure serves to illustrate and describe the claimed invention to aid in the interpretation of the claims. However, this disclosure is not restrictive in character because not every embodiment covered by the claims is necessarily illustrated and described. All changes and modifications that come within the scope of the claims are desired to be protected, not just those embodiments explicitly described.

The invention claimed is:

1. A method for destroying pathogenic cells of a patient, comprising:
    applying a pathogenic cell destroying agent to pathogenic cells localized to a device exposed to a flow of a bodily fluid of the patient, the device having a binding agent attached thereto through a self-assembled molecular monolayer and to which the pathogenic cells are bound or having a roughened surface to which the pathogenic cells are bound, wherein the binding agent comprises an antibody or a ligand that binds specifically to a cell surface protein of the pathogenic cells.

2. The method of claim 1, wherein the bodily fluid is blood, and wherein device has portions that engage a blood vessel wall inside a blood vessel lumen of the patient.

3. The method of claim 1, wherein the device comprises a vascular implant selected from the group consisting of: a vascular filter, a catheter, a wire guide, a stent, a coil, circulating particles, a needle, a graft, and a balloon.

4. The method of claim 1, wherein the device has said binding agent attached thereto through a self-assembled molecular monolayer and to which the pathogenic cells are bound.

5. The method of claim 1, wherein the device comprises a coating comprising an active agent other than the binding agent and wherein the active agent is selected from: chemotherapeutic agents, radiation sensitizing agents, radioprotective agents, anti-restenosis agents, anti-inflammatory agents, antiproliferative agents, pro-healing agents, gene therapy agents, extracellular matrix modulators, anti-thrombotic agents, anti-platelet agents, antiangioplastic agents, antisense agents, anticoagulants, antibiotics, bone morphogenetic proteins, integrins, disintegrins, smooth muscle cell inhibitors, immunosuppressive agents, and anti-antigenic agents.

6. The method of claim 1, wherein the self assembled molecular monolayer comprises a self assembled monolayer of phosphonic acid molecules.

7. The method of claim 1, wherein the pathogenic cells are cancer cells.

8. A medical device, comprising:
    an implant constructed and arranged to be placed within a vessel lumen of a patient;
    a surface to which pathogenic cells circulating in bodily fluid of the patient bind to non-pathogenic cells circulating in bodily fluid of the patient, wherein the surface includes a binding agent attached to the implant through a self-assembled molecular monolayer and which binds to pathogenic cells circulating in bodily fluid of the patient, or wherein the surface is a pathogenic cell binding roughened surface; and
    wherein the binding agent is an antibody or a ligand that binds specifically to a protein on the pathogenic cells.

9. The medical device of claim 8, wherein the implant comprises a frame constructed and arranged to engage a blood vessel wall defining a blood vessel lumen of a patient to secure the position of the implant.

10. The medical device of claim 8, wherein the surface includes said binding agent attached to the implant through a self-assembled molecular monolayer.

11. The medical device of claim 10, wherein the pathogenic cells are cancer cells.

12. The medical device of claim 11, wherein the protein is a cell surface protein.

13. The medical device of claim 8, wherein the binding agent binds specifically to the pathogenic cells.

14. The method of claim 1, comprising said binding agent attached to the device through a self-assembled molecular monolayer and to which the pathogenic cells are bound, and wherein said binding agent comprises a linker.

15. The method of claim 14, wherein the binding agent is an antibody or ligand that binds to MMP-1, MMP-3, MMP-4, MMP-5, MMP-9, MMP-11, VEGFR3, CCR7, CXCR5, CXCR4, Nrp-2, EphA2, HER2, CD96, CD33, CD20, ZAP-70, CD38, CD5, CD23, CD19, CD40, CD45 CD45A, CD21, CD52, CALLA, Tdt, B-lymphocyte stimulator, VEGF, EGFR, SDF protein, Ber-EP4, or CK20.

16. The method of claim 15, wherein the binding agent is an antibody or ligand that binds to EGFR.

17. The method of claim 16, wherein the binding agent is an antibody that binds to EGFR.

18. The method of claim 1, wherein the pathogenic cell destroying agent comprises radiation.

19. The method of claim 18, wherein the radiation is applied from one or more sources external to the patient.

20. The method of claim 18, wherein the radiation is applied intravascularly.

21. The method of claim 2, where only the portions of the device which are not in contact with the vessel wall are coated with said binding agent.

* * * * *